United States Patent
Hareland

(10) Patent No.: US 10,096,105 B2
(45) Date of Patent: Oct. 9, 2018

(54) METHOD OF DETERMINING TARGET TREATMENT LOCATIONS

(71) Applicant: Medtronic, Inc., Minneapolis, MN (US)

(72) Inventor: Scott A. Hareland, Lino Lakes, MN (US)

(73) Assignee: Medtronic CryoCath LP, Toronto, Ontario (CA)

( * ) Notice: Subject to any disclaimer, the term of this patent is extended or adjusted under 35 U.S.C. 154(b) by 134 days.

(21) Appl. No.: 15/259,744

(22) Filed: Sep. 8, 2016

(65) Prior Publication Data
US 2018/0068439 A1     Mar. 8, 2018

(51) Int. Cl.

| G06K 9/00 | (2006.01) |
|---|---|
| G06T 7/00 | (2017.01) |
| G06T 7/60 | (2017.01) |
| G06T 3/60 | (2006.01) |
| G06K 9/62 | (2006.01) |
| A61B 5/02 | (2006.01) |
| A61B 34/20 | (2016.01) |

(52) U.S. Cl.
CPC ........ *G06T 7/0012* (2013.01); *A61B 5/02007* (2013.01); *A61B 34/20* (2016.02); *G06K 9/6215* (2013.01); *G06T 3/60* (2013.01); *G06T 7/004* (2013.01); *G06T 7/60* (2013.01); *G06T 2207/30004* (2013.01)

(58) Field of Classification Search
None
See application file for complete search history.

(56) References Cited

U.S. PATENT DOCUMENTS

| 6,129,669 | A | 10/2000 | Panescu et al. |
|---|---|---|---|
| 6,873,718 | B2 | 3/2005 | O'Donnell et al. |
| 6,926,714 | B1 | 8/2005 | Sra |
| 7,565,190 | B2 | 7/2009 | Okerlund et al. |
| 7,681,579 | B2 | 3/2010 | Schwartz |
| 7,697,972 | B2 | 4/2010 | Verard et al. |
| 7,877,128 | B2 | 1/2011 | Schwartz |
| 8,046,052 | B2 | 10/2011 | Verard et al. |
| 8,285,021 | B2 | 10/2012 | Boese et al. |
| 2005/0256398 | A1 | 11/2005 | Hastings et al. |
| 2007/0152974 | A1 | 7/2007 | Kim et al. |
| 2008/0221425 | A1 | 9/2008 | Olson et al. |
| 2010/0280363 | A1 | 11/2010 | Skarda et al. |

(Continued)

*Primary Examiner* — Matthew Bella
*Assistant Examiner* — Jose M Torres
(74) *Attorney, Agent, or Firm* — Christopher & Weisberg, P.A.

(57) ABSTRACT

A method and system for automatic location of a target treatment structure, such as a pulmonary vein ostium, from an anatomical image. The method includes calculating a most likely path of blood flow through a pulmonary vein based on a cross-sectional area minimization technique and calculating pulmonary vein geometry as a function of length. For example, a pulmonary vein ostium may be located by analyzing a change in pulmonary vein dimensional size or other anatomical factors, such as absolute size. The method may also include determining tissue thickness at the pulmonary vein ostium or other treatment size for treatment dose optimization. The method may be an algorithm performed by a processing unit of a navigation system or other component of a medical system.

18 Claims, 9 Drawing Sheets

(56) References Cited

U.S. PATENT DOCUMENTS

| | | |
|---|---|---|
| 2011/0028848 A1 | 2/2011 | Shaquer et al. |
| 2013/0274712 A1 | 10/2013 | Schecter |
| 2013/0282005 A1 | 10/2013 | Koch et al. |
| 2013/0288218 A1 | 10/2013 | Mallin et al. |
| 2013/0336558 A1 | 12/2013 | Manzke et al. |
| 2014/0276712 A1 | 9/2014 | Mallin et al. |
| 2015/0302584 A1* | 10/2015 | Brauner ............... A61B 6/508 382/128 |
| 2016/0100770 A1* | 4/2016 | Afonso ............... A61B 5/0422 600/515 |

\* cited by examiner

METHOD OF DETERMINING TARGET TREATMENT LOCATIONS

CROSS-REFERENCE TO RELATED APPLICATION n/a

STATEMENT REGARDING FEDERALLY SPONSORED RESEARCH OR DEVELOPMENT n/a

Technical Field

The present invention relates to a method and system for automatically locating target treatment sites, such as pulmonary vein ostia.

Background

In many non-invasive or minimally invasive surgical and treatment procedures, navigating a medical device within a patient's body can be very challenging. Navigation systems are frequently used to help the user identify the location of the medical device and to steer the medical device to the target treatment location. For example, navigation is an important tool in many electrophysiological (EP) procedures because it helps the user understand the placement of the medical device within the cardiac space. Additionally, navigation is often used to place medical devices at areas targeted for thermal treatment and/or ablation.

When the medical device is a focal catheter, for instance, the ablating surface may be directly imaged on the navigation system and there is a close, direct coupling between the navigation and the delivered therapy. However, other medical devices, such as balloon catheters, may have more complex geometry, and navigation electrodes on the device may not exactly correlate with the ablating surface (e.g., the surface of the balloon). Additionally, placement of these complex-geometry devices may be difficult to infer from fluoroscopic imaging or navigation systems relative to the targeted tissue regions.

Ablation of the tissue surrounding one or more pulmonary veins, such as the pulmonary vein ostium, has shown positive results in the treatment of certain types of atrial fibrillation. The success of this treatment, however, largely depends on occlusion of the pulmonary vein with the medical device, which may be difficult to determine using current imaging and navigation techniques, and delivery of the optimal treatment dose, which may depend on tissue thickness at the treatment site, another complicating factor. Additionally, pre-procedural identification of the ablation target sites and subsequent ablation tool selection (e.g., balloon catheter size) can facilitate faster and more predictable procedures prior to invasive interaction with the patient.

SUMMARY

The present invention advantageously provides a method and system for locating a target treatment site. In one embodiment, the system may include a navigation system including a processing unit, the navigation system being configured to store an anatomical image of an area of tissue including the target treatment site, the processing having a processing circuitry with a memory and a processor, the memory in communication with the processor and having instructions that, when executed by the processor, configure the processor to: determine a first center and an inner surface of an anatomical structure, the anatomical structure defining a lumen; determine a first plane that extends across a cross-sectional area of the anatomical structure; determine a first vector that is normal to the first plane and extends from the first center; determine a second vector that lies in the first plane, is normal to the first vector, and extends from the first center; determine a first plurality of distances between the first center and the inner surface of the anatomical structure along the second vector around $2\pi$ radians around the first vector; determine a surface area of a first area defined by an intersection of the first plane and the inner surface of the anatomical structure, the surface area of the first area being based on the first plurality of distances; determine a second center of the anatomical structure, the second center being a predetermined distance along the first vector from the first center; determine a second plane that extends across a cross-sectional area of the anatomical structure, the second center being in the second plane; determine a third vector that is normal to the second plane and extends from the second center; determine a fourth vector that lies in the second plane, is normal to the third vector, and extends from the second center; determine a second plurality of distances between the second center and the inner surface of the anatomical structure along the third vector around $2\pi$ radians around the first vector; determine a surface area of a second area defined by an intersection of the second plane and the inner surface of the anatomical structure, the surface area of the second area being based on the second plurality of distances; and identify a location of the target treatment site based on the determinations. In one embodiment, the processing may be further configured to: before determining the first plurality of distances, rotate the first vector in a first direction by a first amount to define a first adjustment plane and first adjustment vector; calculate a surface area of the first adjustment plane; rotate the first vector in a first direction by a second amount to define a second adjustment plane and second adjustment vector; calculate a surface area of the second adjustment plane; and select one of the first vector, the first adjustment vector, and the second adjustment vector in which the surface area is minimized. In one embodiment, the processor may be further configured to: rotate the first vector in a second direction by a third amount to define a third adjustment plane and third adjustment vector; calculate a surface area of the third adjustment plane; rotate the first vector in a second direction by a fourth amount to define a fourth adjustment plane and fourth adjustment vector; calculate a surface area of the fourth adjustment plane; and select one of the first vector, the third adjustment vector, and the fourth adjustment vector in which the surface area is minimized. In one embodiment, the processor may be further configured to determine an updated first plane and an updated first vector based on the selected adjustment vectors. In one embodiment, the processor may be further configured to determine an updated first center based on the updated first plane, the first plurality of distances being between the updated first center and the inner surface of the anatomical structure. In one embodiment, the processor may be further configured to determine a direction of blood flow within the anatomical structure based at least in part on the first and third vectors. In one embodiment, the processor may be further configured to determine a structure of the anatomical structure based at least in part on the surface area of the first area and the surface area of the second area. In one embodiment, the processor may be further configured to determine a direction of blood flow within the anatomical structure based on the first and third vectors. In one embodiment, the processor may be further configured to determine a structure of the anatomical structure based on the surface area of the first area and the surface area of the second area. In one embodiment the anatomical image may be a segmented image and the segmented image may include an outer surface and an inner surface of the anatomical structure, and the processor may be further configured to determine a thickness of an area of the anatomical structure between the outer surface and the inner surface. In one embodiment, the area of the anatomical structure is the target treatment site. In one embodiment, the anatomical structure is a pulmonary vein and the target treatment site is an ostium of the pulmonary vein. In one embodiment, the system may further include a medical device including at least one treatment element and at least one mapping electrode, the at least one mapping electrode being in communication with the navigation system. In one embodiment, the navigation system may further include a display and at least one navigation electrode. In one embodiment, the processor may be further configured to: determine a target position for the medical device; and displaying to the user the target position of the medical device on the navigation system display.

In one embodiment, a system for locating a target treatment site may include: a processing unit including a processing circuitry including a memory and a processor, the memory in communication with the processor and having instructions that, when executed by the processor, configure the processor to: determine a plurality of planes, each of the plurality of planes having a center and extending across a cross-sectional area of an anatomical structure, the anatomical structure having a lumen and an inner surface, the plurality of planes being over a length of the anatomical structure; determine a plurality of vectors, each of the plurality of vectors extending from the center of a corresponding one of the plurality of planes; calculating a surface area of each of the plurality of planes, the surface area being bounded by the inner surface of the anatomical structure; calculating a difference between surface areas of each pair of adjacent planes of the plurality of planes; identifying a target treatment site based at least in part on the calculated difference. In one embodiment the processor may be further configured to compare a direction of each of the plurality of vectors, the identification of the target treatment site being based at least in part on the comparison. In one embodiment, the processing unit is part of a navigation system, the navigation system being configured to store an anatomical image of an area of tissue including the target treatment site, the determinations being based on the anatomical image. In one embodiment, the anatomical image is a segmented image, the segmented image including an outer surface and an inner surface of the anatomical structure, the processor being further configured to: determine a thickness of an area of the anatomical structure between the outer surface and the inner surface.

In one embodiment, a system for locating a target treatment site may include: a navigation system including a processing unit, the navigation system being configured to store an anatomical image of an area of tissue including the target treatment site, the processing having a processing circuitry with a memory and a processor, the memory in communication with the processor and having instructions that, when executed by the processor, configure the processor to: determine a first center and an inner surface of an anatomical structure, the anatomical structure defining a lumen; determine a first plane that extends across a cross-sectional area of the anatomical structure; determine a first vector that is normal to the first plane and extends from the first center; calculate a surface area of the first plane within an area bounded by the inner surface of the anatomical structure; determine a second vector that lies in the first plane, is normal to the first vector, and extends from the first center; rotate the first vector in a pitch direction by a first amount to define a first adjustment plane and first adjustment vector; calculate a surface area of the first adjustment plane within an area bounded by the inner surface of the anatomical structure; rotate the first vector in the pitch direction by a second amount to define a second adjustment plane and second adjustment vector; calculate a surface area of the second adjustment plane within an area bounded by the inner surface of the anatomical structure; select one of the first vector, the first adjustment vector, and the second adjustment vector in which the surface area is minimized; rotate the first vector in a yaw direction by a third amount to define a third adjustment plane and third adjustment vector; calculate a surface area of the third adjustment plane within an area bounded by the inner surface of the anatomical structure; rotate the first vector in the yaw direction by a fourth amount to define a fourth adjustment plane and fourth adjustment vector; calculate a surface area of the fourth adjustment plane within an area bounded by the inner surface of the anatomical structure; select one of the first vector, the third adjustment vector, and the fourth adjustment vector in which the surface area is minimized; determine an updated first plane and updated first vector based on the selected one of the first vector, first adjustment vector, second adjustment vector, third adjustment vector, and fourth adjustment vector; calculate a surface area of a first area defined by an intersection of the updated first plane and the inner surface of the anatomical structure, the surface area of the first area being based on the first plurality of distances; determine a second center of the anatomical structure, the second center being a predetermined distance along the first vector from the first center; determine a second plane that extends across a cross-sectional area of the anatomical structure, the second center being in the second plane; determine a third vector that is normal to the second plane and extends from the second center; determine a fourth vector that lies in the second plane, is normal to the third vector, and extends from the second center; rotate the third vector in the pitch direction by the first amount to define a fifth adjustment plane and a fifth adjustment vector; calculate a surface area of the fifth adjustment plane within an area bounded by the inner surface of the anatomical structure; rotate the third vector in the pitch direction by the second amount to define a sixth adjustment plane and a sixth adjustment vector; calculate a surface area of the sixth adjustment plane within an area bounded by the inner surface of the anatomical structure; select one of the third vector, the fifth adjustment vector, and the sixth adjustment vector in which the surface area is minimized; rotate the third vector in the yaw direction by the third amount to define a seventh adjustment plane and a seventh adjustment vector; calculate a surface area of the seventh adjustment plane within an area bounded by the inner surface of the anatomical structure; rotate the third vector in the yaw direction by the fourth amount to define an eighth adjustment plane and an eighth adjustment vector; calculate a surface area of the eighth adjustment plane within an area bounded by the inner surface of the anatomical structure; select one of the third vector, the seventh adjustment vector, and the eighths adjustment vector in which the surface area is minimized; determine an updated second plane and an updated second vector based on the selected one of the third vector, fifth adjustment vector, sixth adjustment vector, seventh adjustment vector, and eighth adjustment vector; and identify a location of the target treatment site based on the updated first plane and updated second plane.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
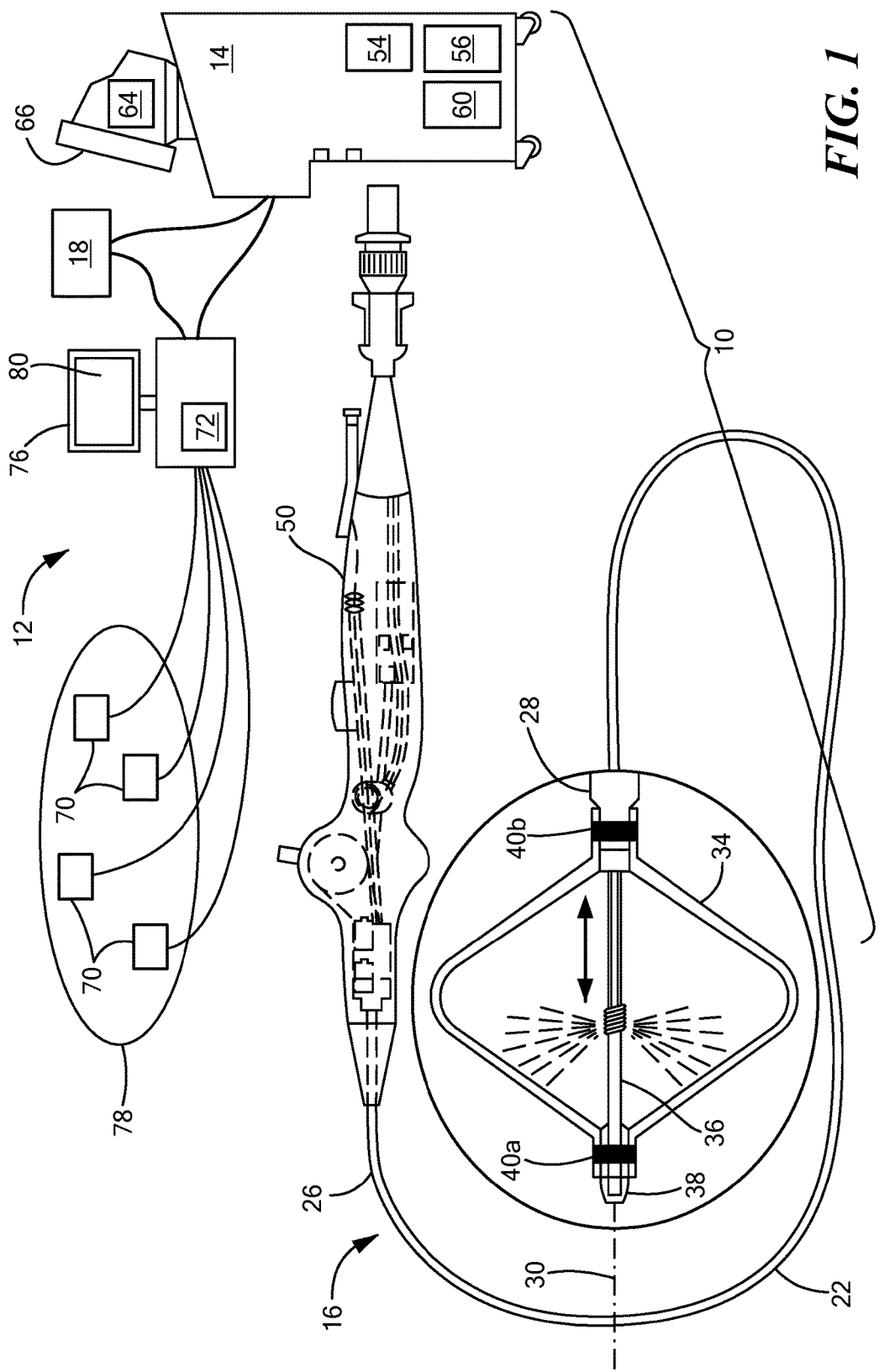
FIG. 1 shows a first exemplary medical system for identifying target treatment locations.

The method and system disclosed herein allows automatic location of a target treatment structure, such as a pulmonary vein ostium, from an anatomical image. The method includes calculating a most likely path of blood flow through a pulmonary vein based on a cross-sectional area minimization technique and calculating pulmonary vein geometry as a function of length. For example, a pulmonary vein ostium may be located by analyzing a change in pulmonary vein dimensional size or other anatomical factors, such as absolute size. The method may also include determining tissue thickness at the pulmonary vein ostium or other treatment size for treatment dose optimization. The method may be an algorithm performed by a processing unit of a navigation system or other component of a medical system.

Before describing in detail exemplary embodiments that are in accordance with the disclosure, it is noted that components have been represented where appropriate by conventional symbols in drawings, showing only those specific details that are pertinent to understanding the embodiments of the disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Figure 2:
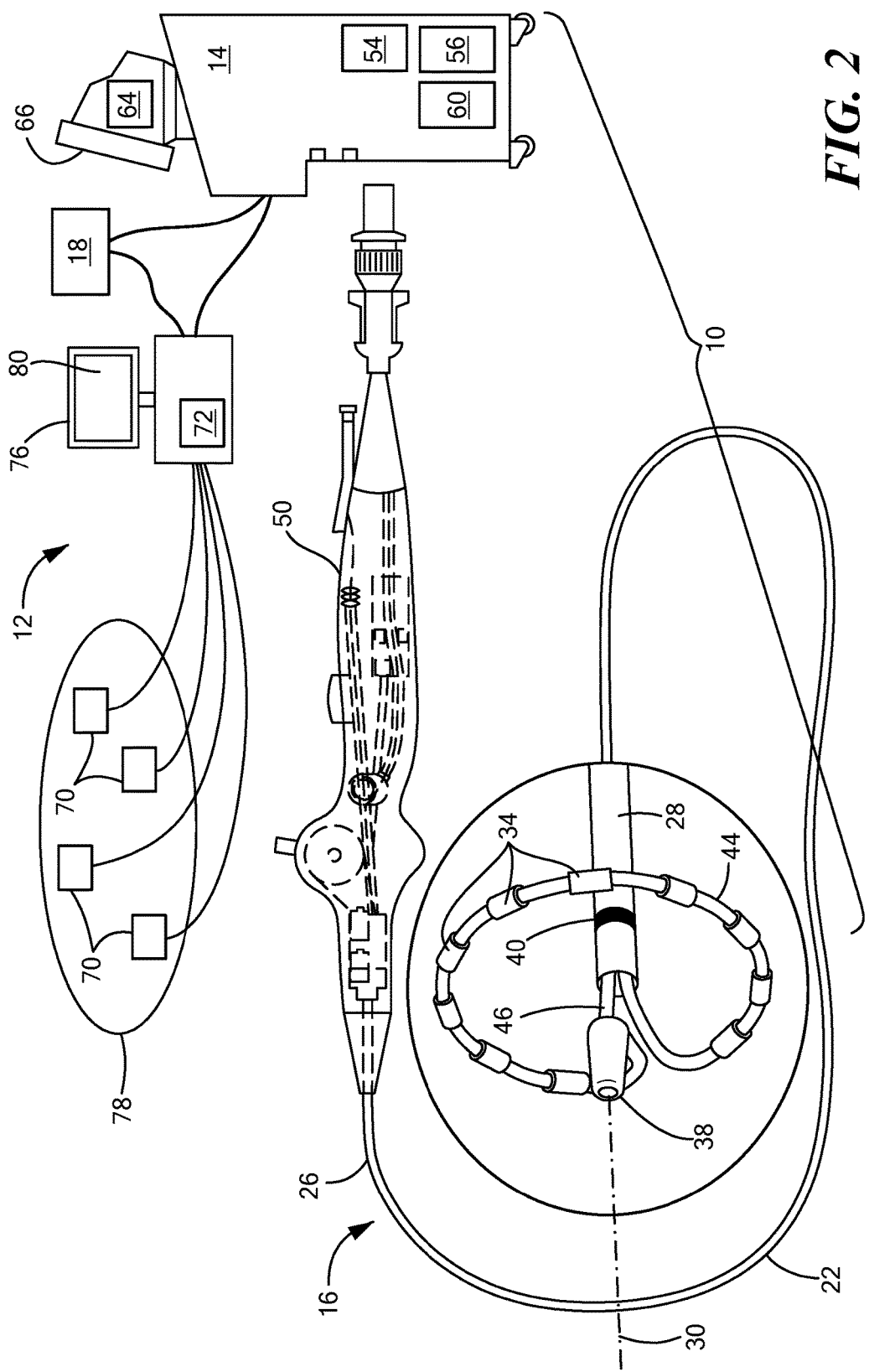
FIG. 2 shows a second exemplary medical system for identifying target treatment locations.

Referring now to the drawing figures in which like reference designations refer to like elements, an embodiment of a medical system constructed in accordance with the principles of the present invention is shown in FIGS. 1 and 2, generally designated as "10." In its simplest form, the system 10 includes a navigation system 12, although the system 10 may also include a control unit 14 or operating console and a medical device 16 in communication with the navigation system 12 and the control unit 14. The system 10 may further include an imaging system 18 for obtaining images of anatomical features within a patient.

The medical device 16 may be a treatment and/or mapping device. The medical device 16 may include an elongate body 22 passable through a patient's vasculature and/or proximate to a tissue region for diagnosis or treatment. For example, the device 16 may be a catheter that is deliverable to the tissue region via a sheath or intravascular introducer (not shown). The elongate body 22 may define a proximal portion 26, a distal portion 28, and a longitudinal axis 30, and may further include one or more lumens disposed within the elongate body 22 thereby providing mechanical, electrical, and/or fluid communication between the elongate body proximal portion 26 and the elongate distal portion 28.

The medical device 16 may further include one or more treatment elements 34 at, coupled to, or on the elongate body distal portion 28 for energetic, therapeutic, and/or investigatory interaction between the medical device 16 and a treatment site or region. The treatment region element(s) 34 may deliver, for example, cryogenic therapy, radiofrequency energy, ultrasound energy, laser energy, or other energetic transfer with a tissue area in proximity to the treatment element(s), including cardiac tissue. For example, the treatment element(s) 34 may include thermally transmissive regions in thermal communication with a coolant or heat source, thermally transmissive regions in electrically communication with a power source, surface therapeutic elements such as surface radiofrequency electrodes, or the like. Additionally, the device 16 may include more than one type of treatment element 34. In the exemplary system shown in FIG. 1, the device 16 may include a treatment element 34 that is expandable, such as one or more balloons. The expandable treatment element 34 may be coupled to a portion of the elongate body distal portion 28. The device 16 may optionally include a shaft 36 that includes a guidewire lumen and is slidably disposed within the elongate body 22 and at least a portion of the shaft 36 may be located within the expandable treatment element 34. The shaft 36 may further include or define a distal tip 38 that may protrude beyond the distal end of the expandable treatment element 34, and which may define an aperture in communication with the guidewire lumen. The expandable treatment element 34 may further include one or more material layers providing for puncture resistance, radiopacity, or the like. If the device 16 is used to delivery cryotherapy (or if used with another energy modality that requires fluid to be delivered to the inner chamber of the treatment element 34), the device may also include one or more fluid injection elements. The device 16 may also include one or more treatment elements in communication with a power source, such as one or more electrodes in communication with a source or radiofrequency energy. Further, if the device 16 is used or mapping in addition to or instead of for the delivery of treatment, the device 16 may include one or more mapping electrodes 40. Although the term "treatment element" is used herein, it will be understood that a mapping element or mapping electrodes could be used instead.

Alternatively, the device 16 may include one or more treatment elements that are not expandable. For example, the device 16 may be a focal catheter that includes one or more electrodes on the distal portion, or may be a device that includes at least one carrier arm bearing one or more treatment electrodes 34 (as shown in the exemplary system of FIG. 2). Each treatment electrode 34 may be considered to be a treatment element. A device having a non-expandable treatment element may also include one or more fluid injection elements within the elongate body 18 proximate the one or more treatment elements (for example, treatment electrode(s)). The device 16 shown in FIG. 2 may include one or more carrier arms 44 that are coupled to a shaft 46 and are transitionable between a first configuration in with each carrier arm 44 is in an at least substantially linear configuration and a second configuration in which each carrier arm 44 is in an expanded configuration.

The device 16 may also include one or more mapping electrodes 40 that are used by the navigation system 12 to visualize the device 16 on a control unit display and/or a navigation system display. For example, the device 16 shown in FIG. 1 may include a first mapping electrode 40*a* distal to the expandable portion of the treatment element 34 and a second mapping electrode 40*b* proximal to the expandable portion of the treatment element 34. Although the mapping electrodes 40*a*, 40*b* are shown as being coupled to the portion of the treatment element 34 that is coupled to the elongate body and/or shaft of the device, the mapping electrodes 40*a*, 40*b* could alternatively be located distal and proximal to all portions of the treatment element, at any location on the device.

Each mapping electrode 40 and treatment element 34 in communication with a power source may be electrically conductive segments for conveying an electrical signal, current, or voltage to a designated tissue region and/or for measuring, recording, receiving, receiving, assessing, or otherwise using one or more electrical properties or characteristics of surrounding tissue or other electrodes. The electrodes may be configured in a myriad of different geometric configurations or controllably deployable shapes, and may also vary in number to suit a particular application, targeted tissue structure or physiological feature.

Although not shown, the system 10 may include one or more sensors to monitor the operating parameters throughout the system, including for example, pressure, temperature, flow rates, volume, power delivery, impedance, or the like in the control unit 14 and/or the medical device 16, in addition to monitoring, recording or otherwise conveying measurements or conditions within the medical device 16 or the ambient environment at the distal portion of the medical device 16. The sensor(s) may be in communication with the control unit 14 for initiating or triggering one or more alerts or therapeutic delivery modifications during operation of the medical device 16. One or more valves, controllers, or the like may be in communication with the sensor(s) to provide for the controlled dispersion or circulation of fluid through the lumens/fluid paths of the medical device 16. Such valves, controllers, or the like may be located in a portion of the medical device 16 and/or in the control unit 14.

The medical device 12 may include a handle 50 coupled to the elongate body proximal portion 26. The handle 50 may include circuitry for identification and/or use in controlling of the medical device 16 or another component of the system. Additionally, the handle 50 may also include connectors that are mateable to the control unit 14 to establish communication between the medical device 16 and one or more components or portions of the control unit 14. The handle 50 may also include one or more actuation or control features that allow a user to control, deflect, steer, or otherwise manipulate a distal portion of the medical device 16 from the proximal portion of the medical device 16. For example, the handle 50 may include one or more components such as a lever or knob for manipulating the elongate body 22 and/or additional components of the medical device 16.

As used herein, the term "control unit 14" for simplicity may include any system components that are not part of the medical device 16 itself, other than components of the navigation system 12 and the imaging system 18, regardless of whether the component is physically located within or external to the control unit 14. Further, the navigation system 12 may be a standalone system in communication with the control unit 14 or may be contained within or integrated with the control unit 14, even though it is shown as being physically separated from the control unit in FIGS. 1 and 2. The control unit 14 may include one or more components for the delivery of one or more energy modalities for which the system is used. For example, if the system 10 is used to deliver cryotherapy, the control unit 14 may include a supply 54 of a fluid such as a coolant, cryogenic refrigerant, or the like, an exhaust or scavenging system for recovering or venting expended fluid for re-use or disposal, as well as various control mechanisms. In addition to providing an exhaust function for the fluid or coolant supply 54, the control unit 14 may also include pumps, valves, controllers or the like to recover and/or re-circulate fluid delivered to the handle 50, the elongate body 20, and/or the fluid pathways of the medical device 16. Further, a vacuum pump 56 in the control unit 14 may create a low-pressure environment in one or more conduits within the medical device 16 so that fluid is drawn into the conduit(s)/lumen(s) of the elongate body 22, away from the distal portion 28 and towards the proximal portion 26 of the elongate body 22.

Additionally or alternatively, the control 14 unit may include an energy source 60 as a treatment or diagnostic mechanism in communication with the treatment element(s) 34 of the medical device 16. The energy source 60 may be a radiofrequency generator having a plurality of output channels, with each channel coupled to an individual treatment electrode 34. The radiofrequency generator 60 may be operable in one or more modes of operation.

The control unit 14 may include one or more controllers, processors, and/or software modules 64 containing processing circuitry configured to execute instructions or algorithms to provide for the automated operation and performance of the features, sequences, calculations, or procedures described herein and/or required for a given medical procedure. Further, the control unit 14 may include one or more user input devices, controllers, and displays 66 for collecting and conveying information from and to the user.

The navigation system 12 may be any commercially available navigation system suitable for use with the control unit 14, device 16, and type of procedure. As a non-limiting example, the navigation system 12 may include a plurality of navigation electrodes 70, a reference electrode (not shown), and a processing unit 72 that collects and processes signals from the device mapping electrodes 40, and a display 76 that displays to the user the location of the device 12 within the patient's body 78 and/or relative to the target anatomical feature (for example, a pulmonary vein ostium), recommended treatment areas, tissue thickness, or the like. The processing unit 72 may include processing circuitry including a memory and a processor, the memory in communication with the processor and having instructions that, when executed by the processor, configure the processor to perform the calculations and determinations discussed herein. Additionally or alternatively, this information may be displayed on the display 66 of the control unit 14. The navigation system 12 may also include an energy source (not shown) for delivering energy to the plurality of navigation electrodes 70. Alternatively, the navigation system 12 may be in communication with the control unit energy source 60. For example, the processing unit 72 may be configured, programmed, or programmable to perform the calculations and make the determinations discussed in greater detail below to identify an anatomical feature and/or a target location for a medical device. Further, the processing unit 72 may execute software and display a software interface 80 with which the user may interact to make a selection, rotate and flag an image, open folders, control the navigation system 12, or the like. As a non-limiting example, the user may interact with the software interface 80 using a touch screen, a keyboard, a mouse, or other input device.

It will be understood that although the navigation system processing unit 72 is disclosed herein as performing the calculations discussed herein, it will be understood that the calculations may additionally or alternatively be performed by one or more processors 64 within the control unit 14.

As shown in FIGS. 1 and 2, the navigation electrodes 70, which may also be referred to as surface electrodes, may be applied to the patient's skin and may deliver relatively low-frequency radiofrequency energy through the patient toward the procedure site, current device location, or the target anatomical feature. The mapping electrode 40 on the device 16 may each record a voltage and impedance from this energy and transmit data to the processing unit 72, which may then determine a position of the mapping electrode 40, and therefore the device 12, within the patient. In addition to impedance-based systems, other navigation electrodes may be used such as magnetic field based, hybrid impedance/magnetic field based, ultrasound field based, and/or radiation based, and/or navigation systems that may be developed in the future.

The processing unit 72 may perform this calculation many times during a procedure, frequently updating the registered location and displaying such to the user so the user can visualize the location of the device relative to the target anatomical feature in real time.

The imaging system 18 may be a computed tomography (CT) system, a magnetic resonance imaging (MRI) system, or other system suitable for creating images of locations within a patient's body. For example, the imaging system may create images in Digital Imaging and Communications in Medicine (DICOM) format. The imaging system 18 may be in communication with and digitally transmit images to the navigation system 12 and/or the control unit 14 for further processing. Alternatively, images recorded by the imaging system 18 may be recorded and transferred to the navigation system 12 and/or the control unit 14 by a user.

Figure 11A:
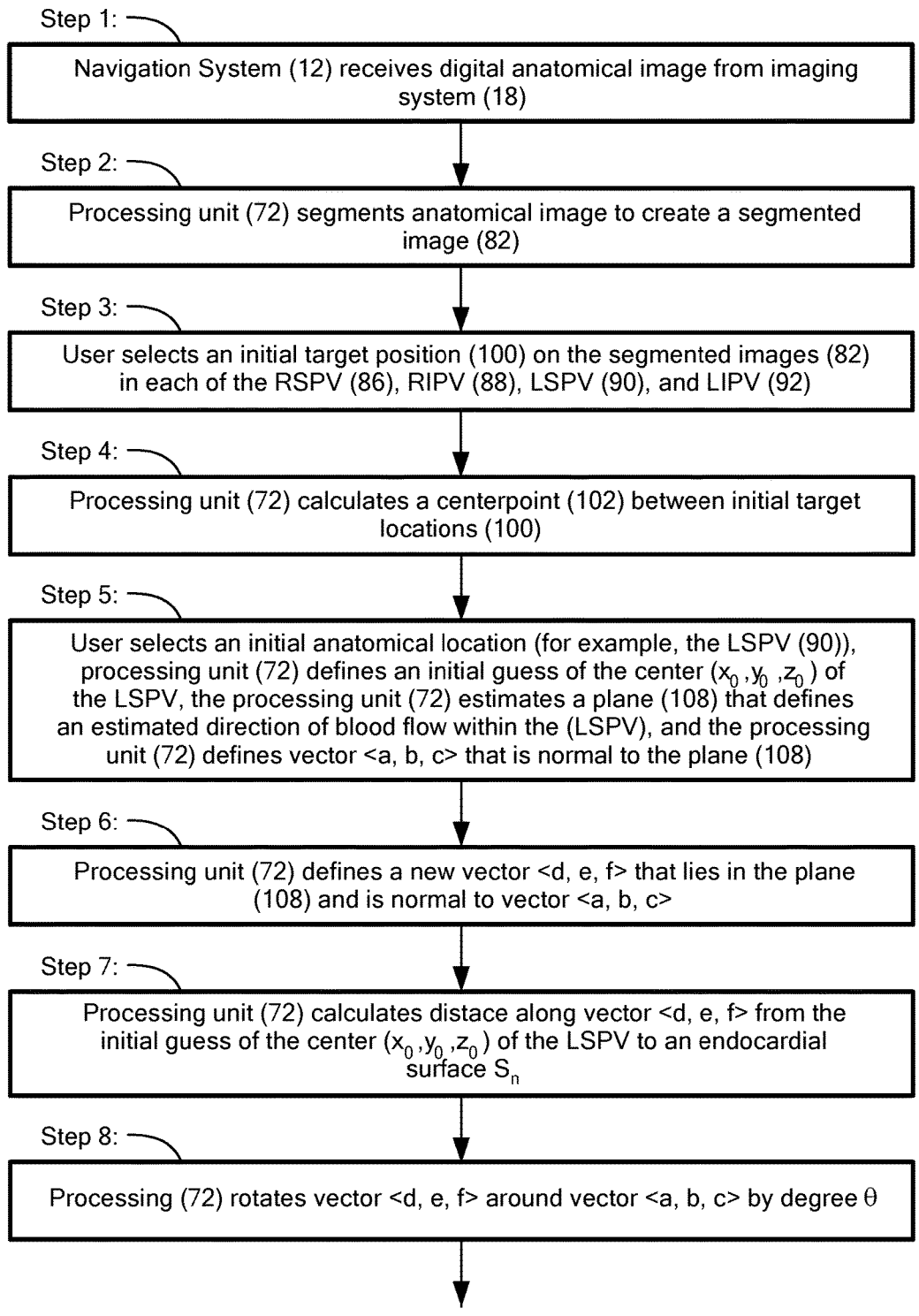
FIGS. 11A-11C show a flow chart of a method for identifying a target tissue location and thickness.
Figure 11B:
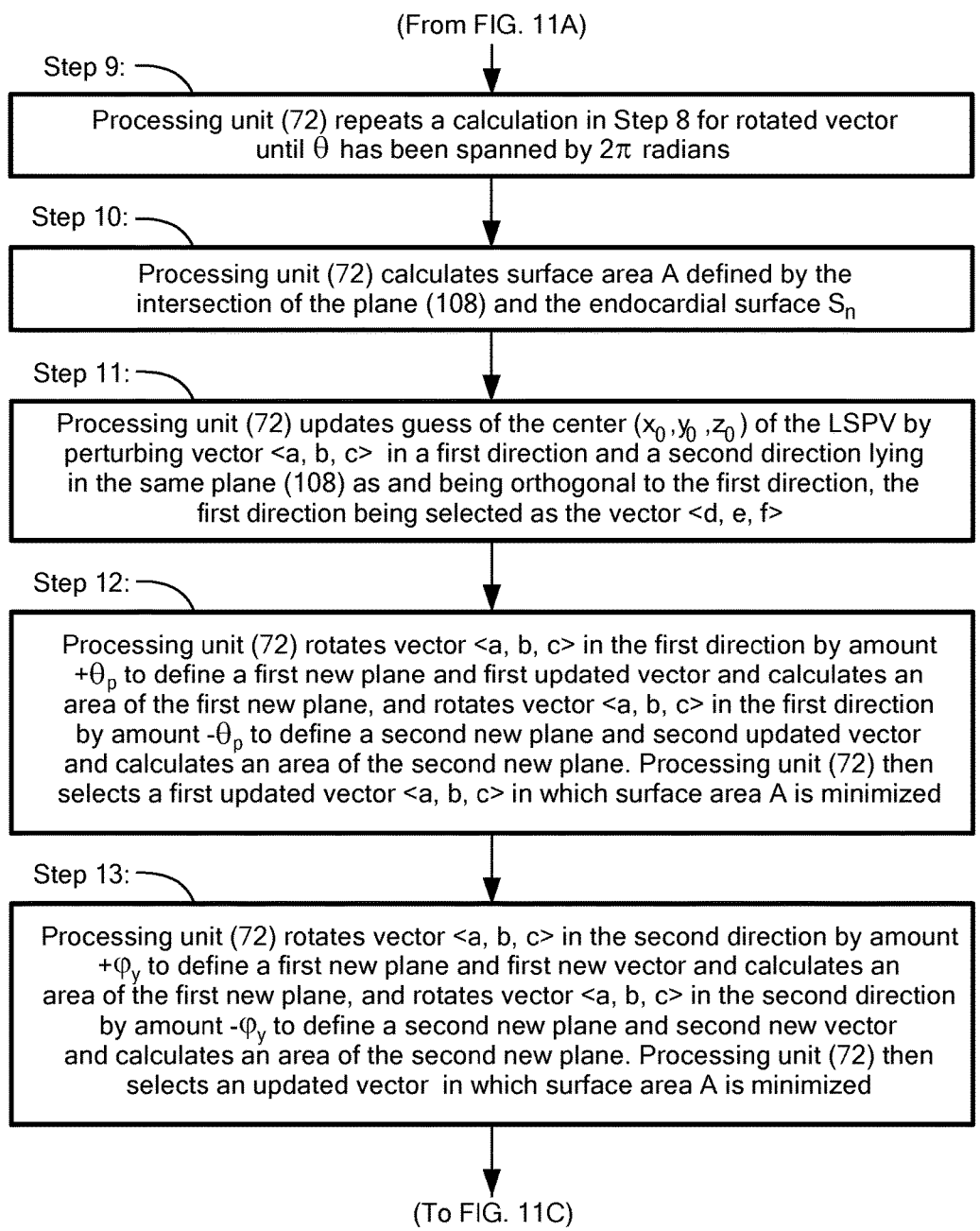
Figure 11C:
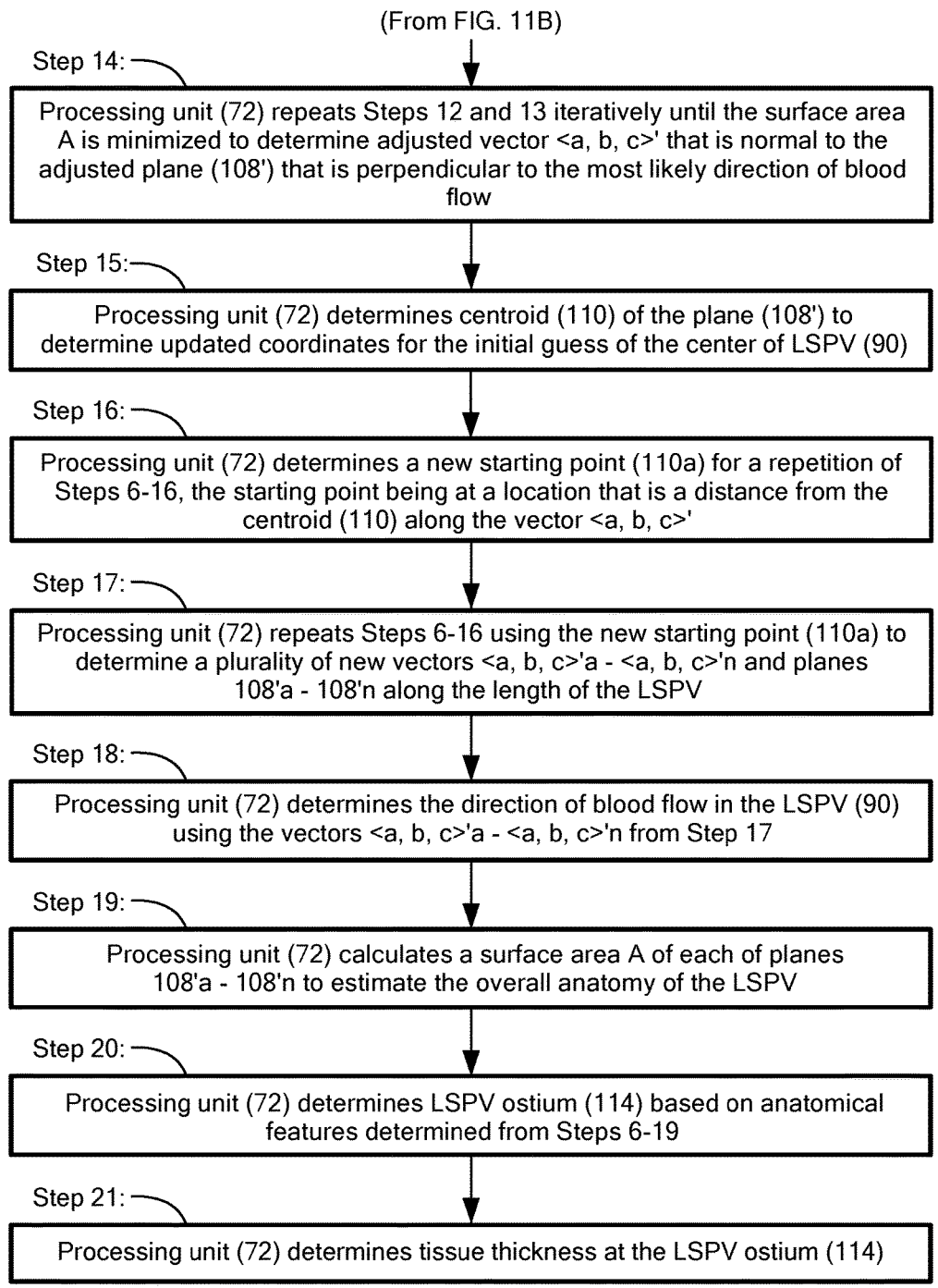

FIGS. 3-10 will now be discussed with reference to the method flowchart shown in FIGS. 11A-11C. The method shown in the flow chart of FIGS. 11A-11C is specific for determining an ostium of a left superior pulmonary vein for purposes of example, but it will be understood that the method disclosed herein may be used to locate target treatment locations in other areas of the patient's body. As non-limiting examples, the method may be used for structures such as the inferior or superior vena cava, the coronary sinus of the right atrium, and other non-cardiac structures. Further, the method may be used to at least substantially tubular anatomical structures, or those structures having a lumen or plenum. Additionally, it will be understood that the elements of FIGS. 3-10 are not drawn to scale and are meant only to show the geometric relationship between components used to locate a target treatment site.

Figure 3:
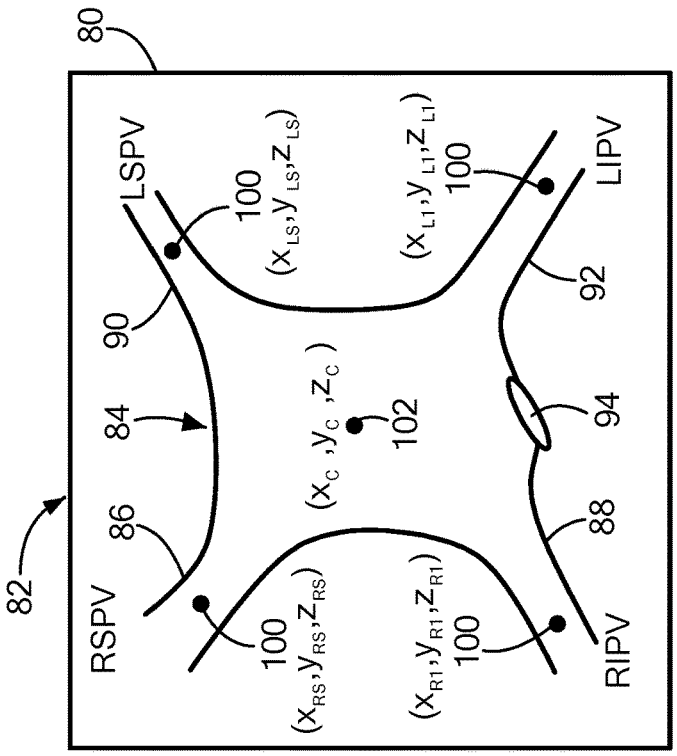
FIG. 3 shows an exemplary display of a segmented image of a left atrium of a heart, with coordinates of initial pulmonary vein locations.

Referring now to FIG. 3, a simplified segmented image of a left atrium of a heart is shown. The navigation system 12 may obtain a digital anatomical image from the imaging system 18 (Step 1 in FIG. 11A). The navigation system 12 may be configured to at least temporarily store and process the anatomical image. Transmission may be wireless, through a wired connection, from a portable data storage device, or the like. FIGS. 1 and 2 show the imaging system 18 as being in communication with the control unit 14 and navigation system 12, but it will be understood that wired connections are optional. The processing unit 72 may then segment the various structures within the digital anatomical image received from the imaging system 18 to identify epicardial and endocardial surfaces of the anatomical feature (Step 2 in FIG. 11A). For example, a segmented image 82 of the left atrium 84 is shown in FIG. 3, although the image may be of any portion of the patient's body. The segmented anatomical image 82, and, optionally, the original anatomical image, may be displayed on the navigation system display 76 and/or the control unit display 66, and the user may be able to interact with the image 82 using the software interface 80. Although the segmented anatomical image 82 shown in FIG. 3 is shown as a line drawing, it will be understood that the segmentation of the anatomical image may also be a three-dimensional image. The left atrium (LA) 84 may include a right superior pulmonary vein (RSPV) 86, a right inferior pulmonary vein (RIPV) 88, a left superior pulmonary vein (LSPV) 90, a left inferior pulmonary vein (LIPV) 92, and a mitral valve 94. In addition, some people have atypical anatomies so additional pulmonary veins, or common pulmonary veins, may be encountered, or some pulmonary veins or other anatomical structures may be missing.

The user may select initial target positions on the segmented image 82 using the software interface 80 (Step 3 in FIG. 11A). As a non-limiting example, the user may select the initial positions 100 of the right superior pulmonary vein (RSPV) 86, the right inferior pulmonary vein (RIPV) 88, the left superior pulmonary vein (LSPV) 90, and the left inferior pulmonary vein (LIPV) 92. As shown in FIG. 3, an initial position 100 within the RSPV may be represented by the coordinates $(x_{RS}, y_{RS}, z_{RS})$, an initial position 100 within the RIPV may be represented by the coordinates $(x_{RI}, y_{RI}, z_{RI})$, an initial position 100 within the LSPV may be represented by the coordinates $(x_{LS}, y_{LS}, z_{LS})$, and an initial position 100 within the LIPV may be represented by the coordinates $(x_{LI}, y_{LI}, z_{LI})$. Reference made herein to coordinates may be to coordinates in a three-dimensional space as defined by the surface electrodes 70 of the navigation system 12 or other reference points in the structure defined by the navigation system.

The processing unit 72 may then calculate a centerpoint 102 within the LA 84 represented by the coordinates $(x_C, y_C, z_C)$ (Step 4 in FIG. 11A). The centerpoint 102 may be equidistant from the initial positions 100 within the RSPV, RIPV, LSPV, and LIPV. The processing unit 72 may calculate the centerpoint 102 according to the following equation:

$$(x_C, y_C, z_C) = [\tfrac{1}{4}(x_{RS}+x_{RI}+x_{LS}+x_{LI}), \tfrac{1}{4}(y_{RS}+y_{RI}+y_{LS}+y_{LI}), \tfrac{1}{4}(z_{RS}+z_{RI}+z_{LS}+z_{LI})] \quad (1)$$

The user may then select a first or initial anatomical location using the software interface 80 (Step 5 of FIG. 11A). Alternatively, the processing unit 72 may automatically choose the first location. For example, a location within a pulmonary vein may be chosen. A first location within each pulmonary vein may be selected in any order, but for illustration the first location within the LSPV may be selected. The processing unit 72 may then define or set an initial guess of the LSPV center 104 coordinates as:

$$(x_0, y_0, z_0) = (x_{LS}, y_{LS}, z_{LS}) \quad (2)$$

and may then estimate a plane abc 108 that defines the direction of blood flow within the LSPV as:

$$a(x-x_0) + b(y-y_0) + c(z-z_0) = 0 \quad (3)$$

where $\langle a, b, c \rangle$ is a vector $\vec{V}_0$ normal to the plane abc 108, with the initial guess of the LSPV center 104 being:

$$\langle a, b, c \rangle = \langle (x_C-x_0), (y_C-y_0), (z_C-z_0) \rangle \quad (4)$$

Figure 4:
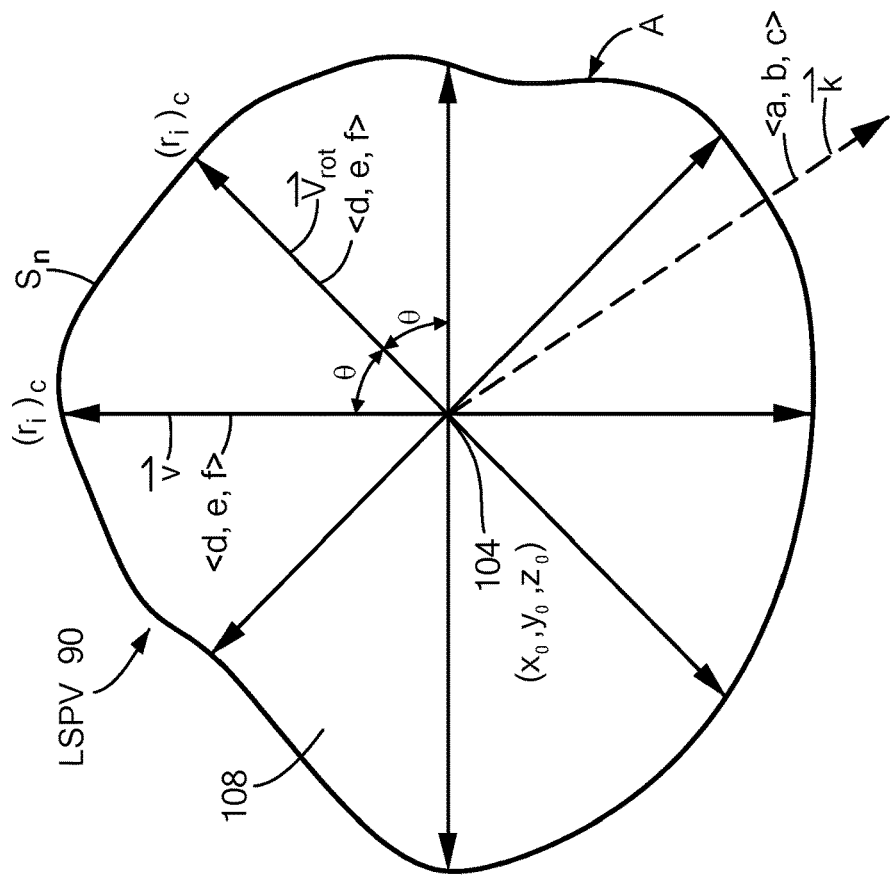
FIG. 4 shows a geometrical representation of a method of determining a surface area of an intersection of a plane abc and an endocardial surface.

As the LSPV is at least substantially tubular (that is, defines a lumen), the LSPV center $(x_0, y_0, z_0)$ is located within the LSPV lumen and not on a portion of tissue. The plane abc 108 may span or extend across the lumen or a cross-sectional area of the LSPV (90), as shown in FIG. 4. As blood flows through the pulmonary veins toward the LA, the vector $\langle a, b, c \rangle$ may extend from LSPV center $(x_0, y_0, z_0)$ toward the LA. Thus, at this stage in the method, vector $\langle a, b, c \rangle$ may represent an initial estimated direction of blood flow through the LA. In the next steps, vector $\langle a, b, c \rangle$ is further defined such that vector $\langle a, b, c \rangle$ defines a plane that has a minimum surface area when measured by the boundary where the plane intersects the anatomical feature (defined by contour $S_n$). For example, the methods described below in Steps 6-15 are one possible approach for determining the direction of flow corresponding to the direction when the plane abc and the anatomical contour $S_n$ comprise a minimum cross-sectional area of the anatomical feature. However, it will be understood that other mathematical algorithms could additionally or alternatively be used to determine the direction of flow, and the methods described in Steps 6-15 may not be the only way to do so.

The processing unit 72 may then identify a vector $\langle d, e, f \rangle$ lying in plane abc 108 (Step 6 in FIG. 11A). The vector $\langle d, e, f \rangle$ may be normal to $\langle a, b, c \rangle$, as $\langle a, b, c \rangle$ is normal to plane abc 108. The vector $\langle d, e, f \rangle$ may be determined by introducing a slight perturbation in two of the directions and calculating the third. For example, the processing unit 72 may select the two directions having the smallest magnitude represented by $\langle a, b, c \rangle$ such that $\hat{x}$ and $\hat{y}$ are selected if $c>a$, $c>b$. For example, small perturbations may be selected around $(x_0, y_0, z_0)$ in the selected directions as in $(x_0+\Delta x, y_0+\Delta y, z_0)$. Given the plane abc 108 and new points $x_0+\Delta x$ and $y_0+\Delta y$, the processing unit 72 may calculate $\Delta z$ such that the following expression is satisfied:

$$\frac{-a(x_0 + \Delta x) - b(y_0 + \Delta y)}{c} - z_0 = \Delta z \quad (5)$$

The vector created by the new point $(\Delta x, \Delta y, \Delta z)$ may lie in the plane abc and be perpendicular to the normal vector $\langle a, b, c \rangle$ with a resulting vector $\langle d, e, f \rangle$ described as:

$$\langle d, e, f \rangle = (x_0, y_0, z_0) + t(\Delta x, \Delta y, \Delta z) \quad (6)$$

Starting at $(x_0, y_0, z_0)$, the processing unit 72 may then increase t until the vector $\langle d, e, f \rangle$ intersects the endocardial surface $S_n$ (for example, an inner wall of the LSPV) (Step 7 in FIG. 11A). The processing unit 72 may record this distance $(r_i)_C$ between the new starting point $(\Delta x, \Delta y, \Delta z)$ and the endocardial surface $S_n$.

Referring now to FIG. 4, the processing unit 72 may then rotate the vector $\langle d, e, f \rangle$ around the vector $\langle a, b, c \rangle$ by a small degree $\theta$ (Step 8 of FIG. 11A). The degree $\theta$ may be fixed or adaptive. The rotation may be calculated according to the following equation (Rodrigues's formula):

$$\vec{V}_{rot} = \vec{V} \cos\theta + (\vec{V} \times \vec{V}) \sin\theta + \vec{V}(\vec{V} \times \vec{V})(1-\cos\theta)$$

where:

$\vec{V} = \langle d, e, f \rangle$ and $\vec{V} = \langle a, b, c \rangle$ and $\vec{V}_{rot}$ is the new rotated vector.

The processing unit 72 may repeat this calculation of $(r_i)_C$ in this rotated vector $\vec{V}_{rot}$ in the new direction from the point $(x_0, y_0, z_0)$ (Step 9 in FIG. 11B).

When $\theta$ has been spanned by $2\pi$ radians, or 360°, the processing unit 72 may calculate the surface area A of an area defined by the intersection of plane abc 108 and the endocardial surface $S_n$ according to the following equation (Step 10 in FIG. 11B):

$$A = \sum_{i=1}^{n} r_i \frac{\theta_{i+1} - \theta_{i-1}}{2} \quad (8)$$

where n is the number of angular sweeps performed by the processing unit 72 in executing the algorithm and $0 \leq \theta_i \leq 2\pi$. The surface area A of an area defined by the intersection of plane abc 108 and the endocardial surface of the pulmonary vein. So, performing this calculation may indicate the shape of the lumen of the pulmonary vein, which may be referred to as the contour, and the cross-sectional size of the pulmonary vein lumen.

Figure 5:
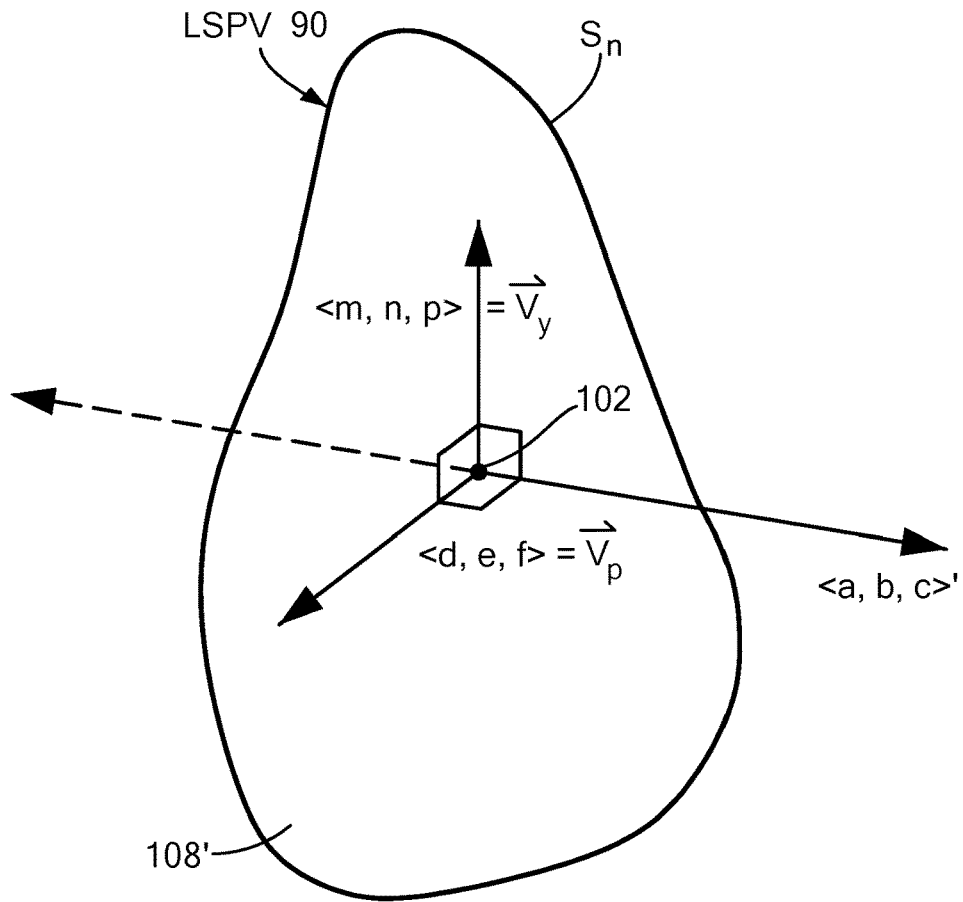
FIG. 5 shows a geometrical representation of vector directions relative to a pulmonary vein.

Referring now to FIG. 5, the processing unit 72 may update the initial guess for the LSPV center ($x_0,y_0,z_0$), and therefore an initial guess for the flow direction vector ⟨a, b, c⟩ by perturbing the vector in two orthogonal directions (Step 11 in FIG. 11). The first orthogonal direction may be referred to as the pitch direction $\vec{V}_p$ and the second orthogonal direction may be referred to as the yaw direction $\vec{v}_y$. Both the pitch and yaw directions may lie in the plane abc and also be orthogonal to each other. The pitch direction may be chosen as the initial vector ⟨d, e, f⟩ calculated previously in the Step 6 of the method. The yaw direction can then be calculated by taking the cross product according to the following equation, or by another equivalent method:

$$⟩a,b,c\,\vec{v}_y \times ⟩d,e,f\,\vec{v}_y = ⟩m,n,p\,\vec{v}_y \quad (9)$$

This new vector ⟩m, n, p $\vec{v}_y$ lies in the plane abc and is perpendicular to both ⟩a, b, c $\vec{v}_y$ and ⟩d, e, f $\vec{v}_y$.

The processing unit 72 may rotate vector ⟩a, b, c $\vec{v}_y$ in the pitch direction by an amount $+\theta_p$ using equation (7) (Step 12 in FIG. 11). This calculation may define a new adjustment plane $(abc)^{i+1}$ and first adjustment vector ⟩a, b, c $\vec{v}_y^{\,i+1}$. The processing unit may repeat the calculation described above, or an equivalent method, to calculate a new area of the adjustment plane $(abc)^{i+1}$ intersecting the endocardial surface $S_n$. The processing unit 72 may then rotate vector ⟩a, b, c $\vec{v}_y$ in the pitch direction by $-\theta_p$ using equation (7) to define a second adjustment plane $(abc)^{i-1}$ and second adjustment vector ⟩a, b, c $\vec{v}_y^{\,i-1}$. The processing unit 72 may then calculate a new area of the second adjustment plane $(abc)^{i-1}$ intersecting the endocardial surface $S_n$, as discussed above. The processing unit 72 may then select the first updated vector ⟩a, b, c $\vec{v}_y$ from the adjustment vectors ⟩a, b, c $\vec{v}_y^{\,i}$ (the original vector ⟩a, b, c $\vec{v}_y$), ⟩a, b, c $\vec{v}_y^{\,i+1}$, and ⟩a, b, c $\vec{v}_y^{\,i-1}$ where the surface area A is minimized (i.e., where the surface area A is smallest). The direction corresponding to the minimum surface area is an estimate for the most likely directly of flow at that point in the anatomical structure.

The processing unit 72 may rotate the updated vector ⟩a, b, c $\vec{v}_y$ according to equation (7) around the yaw direction by an amount of $+\varphi_y$ and $-\varphi_y$ to determine vector ⟩a, b, c $\vec{v}_y^{\,j+1}$ and vector ⟨a, b, c⟩$^{j-1}$, respectively (Step 13 in FIG. 11). The processing unit 72 may then calculate the surface areas $A^{j+1}$ and $A^{j-1}$ in the method described above with the yaw-adjusted planes and the endocardial surface $S_n$. The processing unit 72 may then select the second updated vector ⟨a, b, c⟩ from vectors ⟨a, b, c⟩$^j$, ⟨a, b, c⟩$^{j+1}$, and ⟨a, b, c⟩$^{j-1}$ where the surface area A is minimized.

The processing unit 72 may repeat Steps 12 and 13 iteratively until the surface area A is minimized (Step 14 in FIG. 11). The updated vector ⟨a, b, c⟩' may now be normal to the plane 108' that is perpendicular to the most likely direction of blood flow, the plane being defined as follows:

$$ax+by+cz+d=0 \quad (10)$$

Plane a, b, c 108 and original vector ⟨a, b, c⟩ represented an estimated direction of blood flow through the LSPV. At this stage in the method, however, the direction of blood flow may be more certain and plane a, b, c may be adjusted slightly (the adjusted plane being represented as 108' in FIGS. 5 and 6), meaning that vector ⟨a, b, c⟩ may also be adjusted slightly (the adjusted or updated vector being represented as ⟨a, b, c⟩' in FIGS. 5 and 6).

Figure 6:
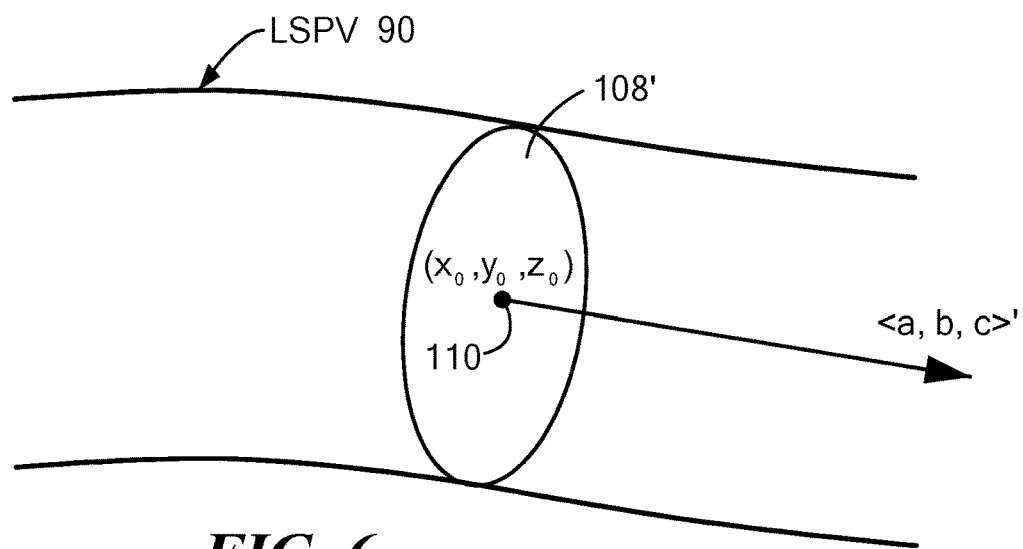
FIG. 6 shows a geometrical representation of a vector relative to a centroid of a first pulmonary vein contour.

Referring now to FIG. 6, the area defined by the contour C, the boundary of the inner surface of the LSPV where intersected by plane abc, may now be defined (Step 15 of FIG. 11). The processing unit 72 may then calculate the centroid 110 of the plane abc 108' constrained by C. As the plane abc 108' constrained by C may not be a perfect circle, this point is referred to as a centroid rather than a center point. Calculation of the centroid 110 may provide updated coordinates for the initial center guess ($x_0,y_0,z_0$) for the LSPV (90).

Figure 7:
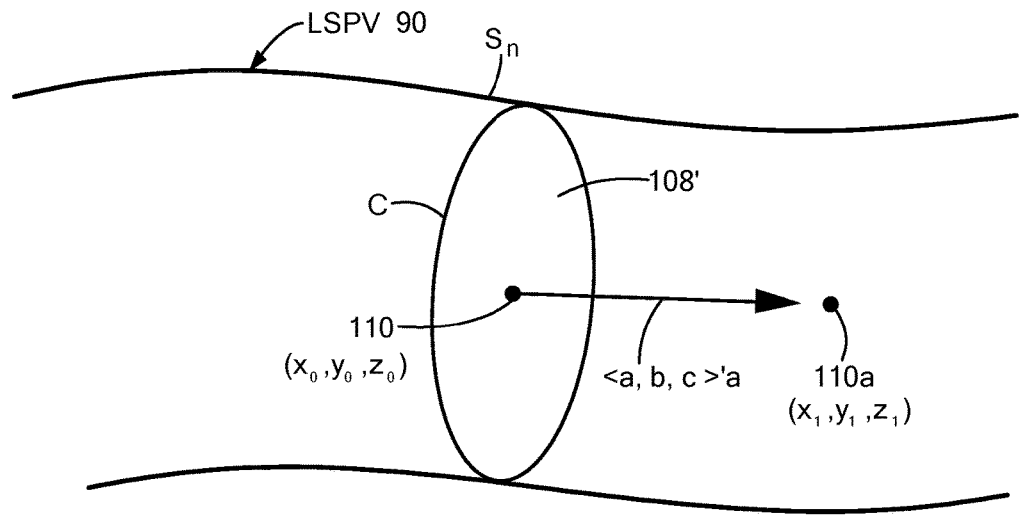
FIG. 7 shows a geometrical representation of determining a centroid of a second pulmonary vein contour.

Referring now to FIG. 7, the processing unit 72 may determine a starting point 110a ($x_1,y_1,z_1$) for the next calculation (Step 16 in FIG. 11). The starting point 110a ($x_1,y_1,z_1$) may be a predetermined or adaptive distance in the direction of vector ⟨a, b, c⟩'a, the coordinates of the location being calculated by the following equation:

$$(x_1,y_1,z_1)=(x_0,y_0,z_0)+t⟨a,b,c⟩ \quad (11)$$

where t indicates a physical distance from $x_0,y_0,z_0$ along the vector ⟨a, b, c⟩.

Figure 8:
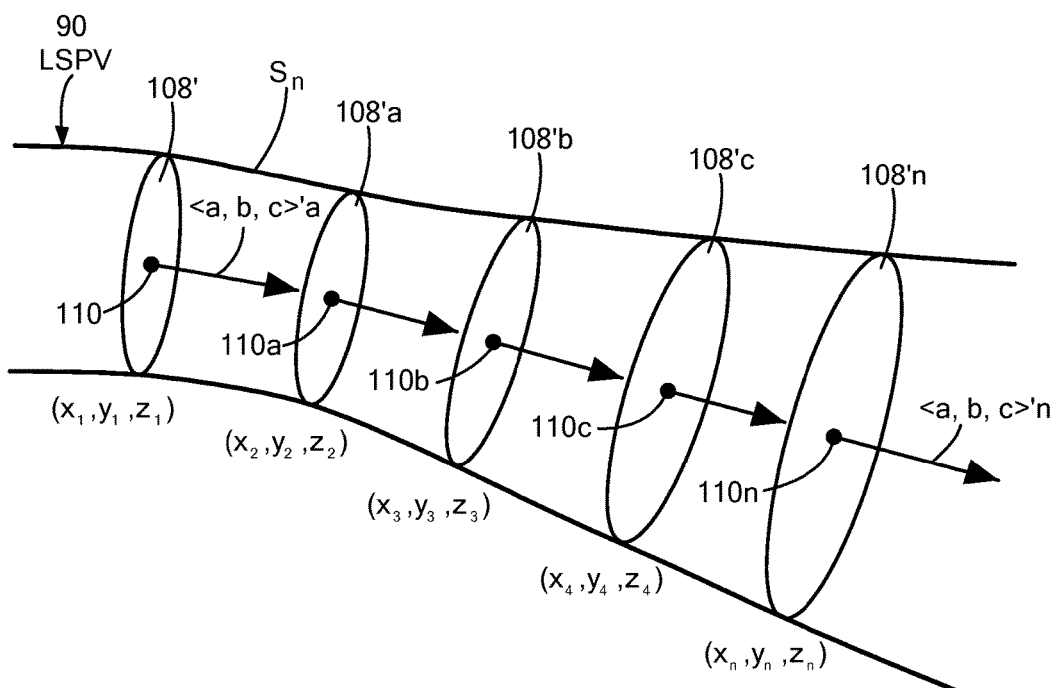
FIG. 8 shows a geometrical representation of a method of determining a plurality of centroids along a length of a pulmonary vein.
Figure 9:
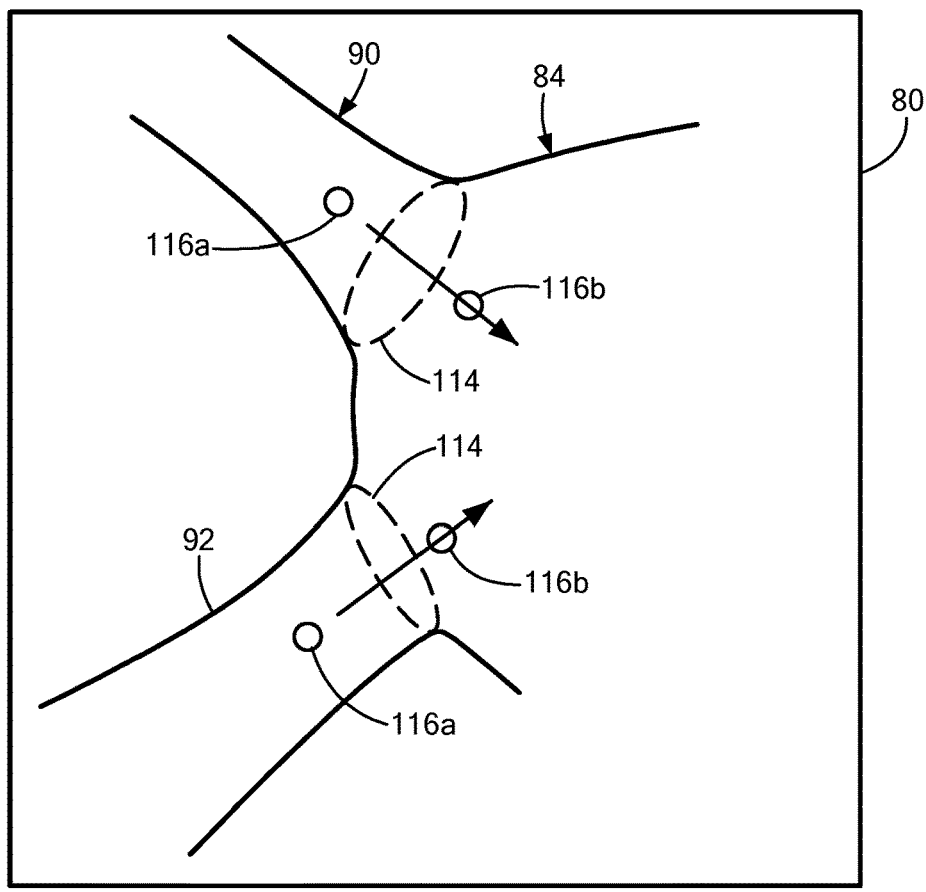
FIG. 9 shows an exemplary display of a portion of a left atrium with recommended target zones identified.
Figure 10:
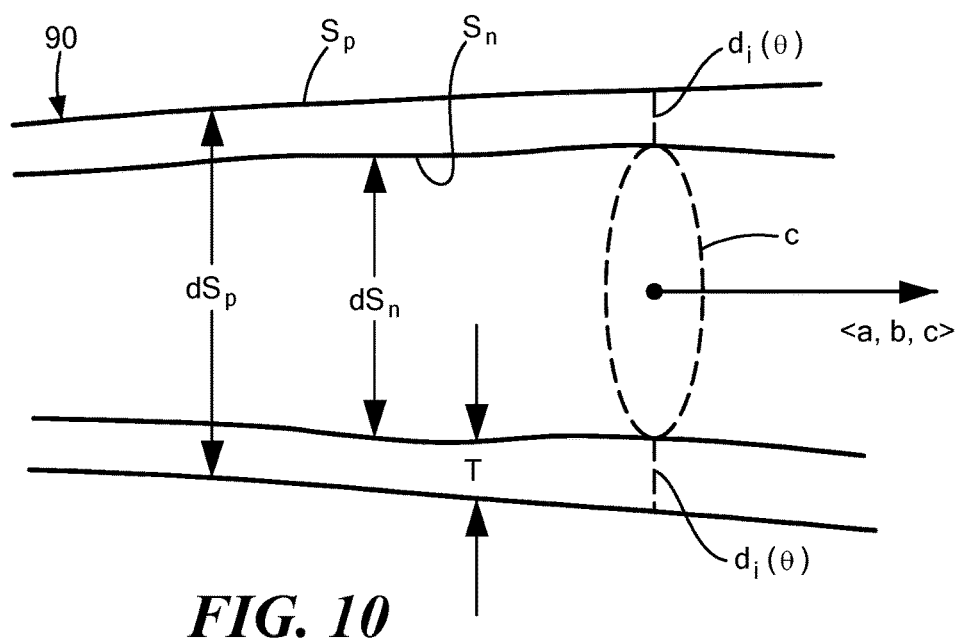
FIG. 10 shows a geometrical representation of a method of determining tissue thickness.

The processing unit 72 may repeat Steps 6 through 16 using the new location 110a ($x_1,y_1,z_1$) as the initial guess of the LSPV center (Step 17 in FIG. 11). These steps may also be repeated a plurality of times using the location coordinates of the previous repetition ($x_n,y_n,z_n$) as the initial guess of the LSPV center. For example, FIG. 8 shows location 110a being defined from location 100 along vector ⟨a, b, c⟩'a using coordinates ($x_1,y_1,z_1$), a new location 110b being defined from location 110a along vector ⟨a, b, c⟩'b using coordinates ($x_2,y_2,z_2$), new location 110c being defined from location 110b along vector ⟨a, b, c⟩'c using coordinates ($x_3,y_3,z_3$), so on until n locations have been defined.

Using this method, the processing unit 72 may calculate the direction of blood flow in each pulmonary vein (Step 18 in FIG. 11). As shown in FIG. 8, the supplemental vectors ⟨a, b, c⟩'a-⟨a, b, c⟩'n determined from the new starting locations 110a-110n may together show an overall direction of blood flow throughout the pulmonary vein.

Further, the areas centered at each centroid point may be used by the processing unit 72 to estimate the cross-sectional area of the pulmonary vein (Step 19 in FIG. 11). In other words, the processing unit 72 may calculate the surface area A for each plane 108'a-108'n. These surface areas A may together indicate the overall anatomy of the LSPV (90).

Finally, the processing unit 72 may determine or estimate the ostium or other ablation target for each pulmonary vein (Step 20 in FIG. 11). These locations may be displayed on the navigation system display and/or the treatment system display. As a non-limiting example, a pulmonary vein ostium 114 may be indicated by the best guess contour based on the determined geometry and/or size of the pulmonary vein, a range of probably locations based on the size of the pulmonary vein, and/or changes in size of the pulmonary vein over distance. For example, a pulmonary vein may have an increasing inner diameter in the direction of blood flow (i.e., toward the left atrium). Accordingly, the processing unit 72 may compare surface areas between pairs of adjacent planes to identify a trend, such as a decreasing or increasing diameter over a length of the pulmonary vein. These features may also be considered in light of the location of the centerpoint 102 in the left atrium 102, as the centerpoint 102 may provide a reference for determining where the ostium may be. The processing unit 72 may reference a table of pulmonary vein measurement data to estimate the location of the ostium 114 based on statistical probability using the features described immediately above.

Additionally, the displayed anatomical features may also be used to determine where a particular treatment device may be used, based on the geometry of the treatment device and the anatomical feature. For example, using the methods described in U.S. Ser. No. 15259683, the entirety of which is incorporated herein by reference, one or more target "landing zones" for treatment elements or other parts of the medical device 16 may be determined and displayed to the user. For example, the processing unit 72 may determine a distal target site 116a and a proximal target site 116b to be used as navigation targets when maneuvering the device 16 to a treatment area.

The success of a treatment may depend on delivering the optimal dose of treatment energy to the target tissue site, which may in turn depend on tissue thickness at the target tissue site. With the pulmonary vein ostium 114 identified, the thickness of the pulmonary vein can be determined by calculating the distance between the endocardial surface $dS_n$, or inner pulmonary vein surface, and the epicardial surface $dS_p$, or outer pulmonary vein surface, along the pulmonary vein ostium identified using the method described above (Step 21 in FIG. 11). Tissue thickness T may be calculated in a plurality of directions from the center of contour C and perpendicular to the vector $\langle a, b, c \rangle$ using the following formula:

$$T = dS_p - dS_n \qquad (12)$$

Further, the pulmonary vein contour C may be swept along pulmonary vein and the calculation made at every location, which may provide an estimate of tissue thickness along the length of the pulmonary vein and at the ostium 114. The calculated thicknesses may be used to determine optimum treatment energy dose. As a non-limiting example, if cryoablation is used, the control unit 14 may adjust the temperature of the treatment element(s) 34 and/or treatment time such that thicker tissue is treated at a lower temperature and/or for a longer period of time than thinner tissue.

As will be appreciated by one of skill in the art, certain concepts described herein may be embodied as a method, data processing system, and/or computer program product. Accordingly, these concepts described herein may take the form of an entirely hardware embodiment, an entirely software embodiment or an embodiment combining software and hardware aspects. Furthermore, the disclosure may take the form of a computer program product on a tangible computer usable storage medium having computer program code embodied in the medium that can be executed by a computer. Any suitable tangible computer readable medium may be utilized including hard disks, CD-ROMs, electronic storage devices, optical storage devices, or magnetic storage devices.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for locating a target treatment site, the system comprising:
    a navigation system including a processing unit, the navigation system being configured to store an anatomical image of an area of tissue including the target treatment site, the processing having a processing circuitry with a memory and a processor, the memory in communication with the processor and having instructions that, when executed by the processor, configure the processor to:
       determine a first center and an inner surface of an anatomical structure, the anatomical structure defining a lumen;
       determine a first plane that extends across a cross-sectional area of the anatomical structure;
       determine a first vector that is normal to the first plane and extends from the first center;
       determine a second vector that lies in the first plane, is normal to the first vector, and extends from the first center;
       determine a first plurality of distances between the first center and the inner surface of the anatomical structure along the second vector around $2\pi$ radians around the first vector;
       determine a surface area of a first area defined by an intersection of the first plane and the inner surface of the anatomical structure, the surface area of the first area being based on the first plurality of distances;
       determine a second center of the anatomical structure, the second center being a predetermined distance along the first vector from the first center;
       determine a second plane that extends across a cross-sectional area of the anatomical structure, the second center being in the second plane;
       determine a third vector that is normal to the second plane and extends from the second center;
       determine a fourth vector that lies in the second plane, is normal to the third vector, and extends from the second center;
       determine a second plurality of distances between the second center and the inner surface of the anatomical structure along the third vector around $2\pi$ radians around the first vector;
       determine a surface area of a second area defined by an intersection of the second plane and the inner surface of the anatomical structure, the surface area of the second area being based on the second plurality of distances; and
       identify a location of the target treatment site based on the determinations.

2. The system of claim 1, wherein the processor is further configured to:
    before determining the first plurality of distances, rotate the first vector in a first direction by a first amount to define a first adjustment plane and first adjustment vector;
    calculate a surface area of the first adjustment plane;
    rotate the first vector in a first direction by a second amount to define a second adjustment plane and second adjustment vector;
    calculate a surface area of the second adjustment plane; and
    select one of the first vector, the first adjustment vector, and the second adjustment vector in which the surface area is minimized.

3. The system of claim 2, wherein the processor is further configured to:
    rotate the first vector in a second direction by a third amount to define a third adjustment plane and third adjustment vector;
    calculate a surface area of the third adjustment plane;
    rotate the first vector in a second direction by a fourth amount to define a fourth adjustment plane and fourth adjustment vector;

calculate a surface area of the fourth adjustment plane; and
select one of the first vector, the third adjustment vector, and the fourth adjustment vector in which the surface area is minimized.

4. The system of claim 3, wherein the processor is further configured to:
determine an updated first plane and updated first vector based on the selected adjustment vectors.

5. The system of claim 4, wherein the processor is further configured to:
determine an updated first center based on the updated first plane, the first plurality of distances being between the updated first center and the inner surface of the anatomical structure.

6. The system of claim 5, wherein the processor is further configured to:
determine a direction of blood flow within the anatomical structure based at least in part on the first and third vectors.

7. The system of claim 6, wherein the processor is further configured to:
determine a structure of the anatomical structure based at least in part on the surface area of the first area and the surface area of the second area.

8. The system of claim 1, wherein the processor is further configured to:
determine a direction of blood flow within the anatomical structure based on the first and third vectors.

9. The system of claim 8, wherein the processor is further configured to:
determine a structure of the anatomical structure based on the surface area of the first area and the surface area of the second area.

10. The system of claim 1, wherein the anatomical image is a segmented image, the segmented image including an outer surface and an inner surface of the anatomical structure, the processor being further configured to:
determine a thickness of an area of the anatomical structure between the outer surface and the inner surface.

11. The system of claim 10, wherein the area of the anatomical structure is the target treatment site.

12. The system of claim 11, wherein the anatomical structure is a pulmonary vein and the target treatment site is an ostium of the pulmonary vein.

13. The system of claim 1, wherein the system further comprising:
a medical device including at least one treatment element and at least one mapping electrode, the at least one mapping electrode being in communication with the navigation system.

14. The system of claim 13 wherein the navigation system further includes:
a display; and
at least one navigation electrode.

15. The system of claim 14, wherein the processor is further configured to:
determine a target position for the medical device; and
displaying to the user the target position of the medical device on the navigation system display.

16. A system for locating a target treatment site, the system comprising:
a processing unit including a processing circuitry including a memory and a processor, the memory in communication with the processor and having instructions that, when executed by the processor, configure the processor to:

determine a plurality of planes, each of the plurality of planes having a center and extending across a cross-sectional area of an anatomical structure, the anatomical structure having a lumen and an inner surface, the plurality of planes being over a length of the anatomical structure;
determine a plurality of vectors, each of the plurality of vectors extending from the center of a corresponding one of the plurality of planes;
calculate a surface area of each of the plurality of planes, the surface area being bounded by the inner surface of the anatomical structure;
calculate a difference between surface areas of each pair of adjacent planes of the plurality of planes;
identify a target treatment site based at least in part on the calculated difference
the processing unit being part of a navigation system, the navigation system being configured to store an anatomical image of an area of tissue including the target treatment site, the determinations being based on the anatomical image, the anatomical image being a segmented image including an outer surface and an inner surface of the anatomical structure, the processor being further configured to:
determine a thickness of an area of the anatomical structure by calculating a distance between the outer surface and the inner surface; and
determine an optimal treatment energy dose for delivery at the target treatment site, the determined optimal treatment energy dose being based at least in part on the determined thickness.

17. The system of claim 16, wherein the processing is further configured to:
compare a direction of each of the plurality of vectors, the identification of the target treatment site being based at least in part on the comparison.

18. A system for locating a target treatment site, the system comprising:
a navigation system including a processing unit, the navigation system being configured to store an anatomical image of an area of tissue including the target treatment site, the processing having a processing circuitry with a memory and a processor, the memory in communication with the processor and having instructions that, when executed by the processor, configure the processor to:
determine a first center and an inner surface of an anatomical structure, the anatomical structure defining a lumen;
determine a first plane that extends across a cross-sectional area of the anatomical structure;
determine a first vector that is normal to the first plane and extends from the first center;
calculate a surface area of the first plane within an area bounded by the inner surface of the anatomical structure;
determine a second vector that lies in the first plane, is normal to the first vector, and extends from the first center;
rotate the first vector in a pitch direction by a first amount to define a first adjustment plane and first adjustment vector;
calculate a surface area of the first adjustment plane within an area bounded by the inner surface of the anatomical structure;
rotate the first vector in the pitch direction by a second amount to define a second adjustment plane and second adjustment vector;

calculate a surface area of the second adjustment plane within an area bounded by the inner surface of the anatomical structure;
select one of the first vector, the first adjustment vector, and the second adjustment vector in which the surface area is minimized;
rotate the first vector in a yaw direction by a third amount to define a third adjustment plane and third adjustment vector;
calculate a surface area of the third adjustment plane within an area bounded by the inner surface of the anatomical structure;
rotate the first vector in the yaw direction by a fourth amount to define a fourth adjustment plane and fourth adjustment vector;
calculate a surface area of the fourth adjustment plane within an area bounded by the inner surface of the anatomical structure;
select one of the first vector, the third adjustment vector, and the fourth adjustment vector in which the surface area is minimized;
determine an updated first plane and updated first vector based on the selected one of the first vector, first adjustment vector, second adjustment vector, third adjustment vector, and fourth adjustment vector;
calculate a surface area of a first area defined by an intersection of the updated first plane and the inner surface of the anatomical structure, the surface area of the first area being based on the first plurality of distances;
determine a second center of the anatomical structure, the second center being a predetermined distance along the first vector from the first center;
determine a second plane that extends across a cross-sectional area of the anatomical structure, the second center being in the second plane;
determine a third vector that is normal to the second plane and extends from the second center;
determine a fourth vector that lies in the second plane, is normal to the third vector, and extends from the second center;
rotate the third vector in the pitch direction by the first amount to define a fifth adjustment plane and a fifth adjustment vector;
calculate a surface area of the fifth adjustment plane within an area bounded by the inner surface of the anatomical structure;
rotate the third vector in the pitch direction by the second amount to define a sixth adjustment plane and a sixth adjustment vector;
calculate a surface area of the sixth adjustment plane within an area bounded by the inner surface of the anatomical structure;
select one of the third vector, the fifth adjustment vector, and the sixth adjustment vector in which the surface area is minimized;
rotate the third vector in the yaw direction by the third amount to define a seventh adjustment plane and a seventh adjustment vector;
calculate a surface area of the seventh adjustment plane within an area bounded by the inner surface of the anatomical structure;
rotate the third vector in the yaw direction by the fourth amount to define an eighth adjustment plane and an eighth adjustment vector;
calculate a surface area of the eighth adjustment plane within an area bounded by the inner surface of the anatomical structure;
select one of the third vector, the seventh adjustment vector, and the eighths adjustment vector in which the surface area is minimized;
determine an updated second plane and an updated second vector based on the selected one of the third vector, fifth adjustment vector, sixth adjustment vector, seventh adjustment vector, and eighth adjustment vector; and
identify a location of the target treatment site based on the updated first plane and updated second plane.

\* \* \* \* \*